(12) United States Patent
Karra et al.

(10) Patent No.: US 11,621,061 B2
(45) Date of Patent: Apr. 4, 2023

(54) PROACTIVE CLINICAL CHECKING FOR COMPUTERIZED PHYSICIAN ORDER ENTRY (CPOE) SYSTEMS

(71) Applicant: CERNER INNOVATION, INC., Kansas City, KS (US)

(72) Inventors: Damodar Reddy Karra, Bangalore (IN); Antony Raymond, Bangalore (IN)

(73) Assignee: CERNER INNOVATION, INC., Kansas City, MO (US)

( * ) Notice: Subject to any disclaimer, the term of this patent is extended or adjusted under 35 U.S.C. 154(b) by 181 days.

(21) Appl. No.: 16/213,350

(22) Filed: Dec. 7, 2018

(65) Prior Publication Data

US 2020/0185065 A1 Jun. 11, 2020

(51) Int. Cl.
G16H 10/60 (2018.01)
G06F 16/93 (2019.01)

(52) U.S. Cl.
CPC .............. *G16H 10/60* (2018.01); *G06F 16/93* (2019.01)

(58) Field of Classification Search
CPC ........ G16H 10/60; G16H 50/30; G16H 40/63; G16H 40/20; G16H 20/10; G06F 16/93
See application file for complete search history.

(56) References Cited

U.S. PATENT DOCUMENTS

| | | | |
|---|---|---|---|
| 7,779,003 B2 | 8/2010 | McKnight | |
| 7,904,314 B2 | 3/2011 | Brandt | |
| 8,160,895 B2 | 4/2012 | Schmitt et al. | |
| 8,224,671 B2 | 7/2012 | Nedblake et al. | |
| 8,265,948 B2 | 9/2012 | Schmitt et al. | |
| 8,498,880 B2 | 7/2013 | Nedblake et al. | |
| 8,924,224 B2 | 12/2014 | Hoffman et al. | |
| 9,104,391 B2 | 8/2015 | DeHaan | |
| 10,037,411 B2 | 7/2018 | Bala et al. | |
| 2004/0153341 A1 | 8/2004 | Brandt et al. | |
| 2005/0015279 A1 | 1/2005 | Rucker et al. | |
| 2009/0106333 A1 | 4/2009 | Nedblake et al. | |
| 2009/0112934 A1 | 4/2009 | Nedblake et al. | |
| 2010/0106529 A1* | 4/2010 | McCallie | G16H 20/10 705/3 |
| 2010/0169771 A1 | 7/2010 | Pelegrin et al. | |

(Continued)

OTHER PUBLICATIONS

A Primer on Physician Order Entry by the California Healthcare Foundation, First Consulting Group, Sep. 2000 (Year: 2000).*

*Primary Examiner* — Rachelle L Reichert
(74) *Attorney, Agent, or Firm* — Kraguljac Law Group, LLC (57) ABSTRACT

Methods and computer systems are provided for issuing or suppressing patient alerts prior to order entry. In some embodiments, alert information is provided prior to a user placing an order, based on proactive clinical checking prior to ordering, thereby avoiding the need to change or cancel orders later. In some cases, proactive clinical checking uses data regarding physicians or other medical professionals, and/or patients, to determine whether or not an alert should be issued that requires a user to accept or override an alert. In embodiments, alert information may still be displayed but, based on dynamic rules, the alert may not require a response from a user. The providing of alerts prior to ordering, or the suppressing of alerts based on data, can address alert fatigue by users and improve patient care.

20 Claims, 7 Drawing Sheets

(56) References Cited

U.S. PATENT DOCUMENTS

2013/0304482 A1\* 11/2013 Siddiqui ................ G16H 10/60
                                                                705/2
2015/0193583 A1   7/2015 McNair et al.
2015/0227689 A1   8/2015 Taylor et al.
2017/0124269 A1   5/2017 McNair et al.

\* cited by examiner

FIG. 1

| Patient Age (Y) | Patient Diagnoses | Patient Problems | Treatment | Medication/ Therapy | Reported Side-effects ||| Effectiveness Score |
|---|---|---|---|---|---|---|---|---|
| | | | | | Major | Moderate | Minor | |
| A | A12.345Z | 449890002 | T1 | Med1 | 0 | 0 | 1 | 10 |
| | | | | Med2 | 0 | 1 | 0 | |
| | | | | Med3 | 0 | 0 | 0 | |
| B | A34.567P | 272060000 | T1 | Med1 | 0 | 1 | 1 | 7 |
| | | | | Med2 | 0 | 0 | 0 | |
| C | A56.789E | 224960004 | T1 | Med1 | 0 | 0 | 0 | 9 |
| | | | | Med2 | 0 | 0 | 1 | |
| | | 282965002 | T2 | Med3 | 1 | 0 | 0 | 5 |
| | | | | Med4 | 0 | 0 | 0 | |
| | C12.605F | 70944005 | T3 | Med5 | 0 | 0 | 0 | 10 |
| | | | | Med6 | 0 | 0 | 0 | |
| * | * | * | * | * | * | * | * | * |
| * | * | * | * | * | * | * | * | * |

FIG. 2

| User ─324 | Medication/Therapy ─336 | Alert Category ─344 ─348 ─352 | Alert Severity ─364 | User Response ─376 ─320 ─314 ─316 |
|---|---|---|---|---|
| P1 | Med1 }332 | Drug-Allergy Interaction | 3 }368 | A }380 |
| P1 | Med2 }340 | Drug-Allergy Interaction | 2 }372 | O }384 |
| P2 | Med1 | Drug-Allergy Interaction | 1 | O |
| P2 | Med3 ─356 | Drug-drug Interaction | 3 | A |
| P3 | Med2 | Drug-drug Interaction | 2 | O |
| P3 | Med5 | Drug-drug Interaction | 1 | O |
| P4 | Med1 ─360 | Dosage Checking | 3 | O |
| P4 | Med6 | Dosage Checking | 2 | O |
| P5 | Med10 | Dosage Checking | 1 | O |
| * | * | * | * | * |
| * | * | * | * | * |
| * | * | * | * | * |

| Place Order | |
|---|---|
| Search [amo] 🔍 | |
| Amoxapine 25mg, Tab, Oral, TID  810 | Alert Information |
| Amoxapine 50mg, Tab, Oral, TID | Drug-drug Interaction ~818 |
| Amoxicillin 250mg, Cap, Oral TID 👆 | |
| Amoxicillin 50mg/mL, Oral Liquid | Reason: The drug amoxicillin will have ~822 |
| *Amoxicot* | interaction with methotrexate which is already |
| Amoxil 250mg, Cap, oral, TID | present in the patient active medication list. |
| | Interactions/Side-effects: <List of side-effects> ~826 |
| | References/Education: <may provide |
| | hyperlink related to relevant articles for ~830 |
| | references> |
| | Past Alert Response: Accepted ~834 |

814 (brace encompassing alert information section)

FIG. 8

PROACTIVE CLINICAL CHECKING FOR COMPUTERIZED PHYSICIAN ORDER ENTRY (CPOE) SYSTEMS

BACKGROUND

Typical systems for providing alerts relating to medical patients, such as computerized physician order entry (CPOE) systems associated with clinical decision support (CDS) systems, use static rules. Rules may include static rules for identifying potential interactions, for example drug-drug interactions or drug-allergy interactions, or contraindications or dosage rules. The rules do not consider requests or orders relating to a patient in context or in view of prior actions. A medical professional such as a physician may be required to return to and change an order to provide context, or to override alerts, which can contribute to lapses in patient care or hazards to patients.

These systems check for and display alerts only when users select or place orders or requests relating to a patient. Therefore, systems are reactive to user actions. Systems may also cause alert fatigue because they do not reduce the number of system prompts or alerts or eliminate the need for user response in some cases. In some cases, vital alerts relating to patient care may be missed because of alert fatigue, rendering systems ineffective and endangering patients. Healthcare information technology systems relating to electronic medical and health records can generate too many alerts, and the alerts can occur at later points in a workflow, which reduces the effectiveness of the system.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-storage media for providing or suppressing patient alerts. For example, in embodiments, the system receives an indication that a user has selected one or more characters in association with a search screen, wherein the search screen is part of a computerized physician order entry system, and performs a search for a first set of potential orders for a first patient based on the one or more characters. Then the system performs a first check based on the first set of potential orders and provides search results to the user, prior to the entry of an order by the user, wherein the search results include one or more indicators of interactions. In some cases, performing a first check includes considering a first set of patient data associated with the first patient, or the first set of patient data includes one or more current orders associated with the first patient. In embodiments, one or more current orders are analyzed for a first set of interactions, or one or more indicators of interactions includes a color-coding associated with one or more of the search results. In some cases, the system receives a selection by the user that causes the display of the interactions. In embodiments, performing a first check includes considering alert response data.

In other embodiments, a computer-implemented method of suppressing patient alerts includes receiving an indication that a first interaction has been detected for a first patient, receiving a first rule associated with the first interaction, and applying the first rule to the first interaction. The method can include suppressing an alert for the first interaction, wherein the alert requires a user to respond to a notification associated with the alert. In some cases, the first rule is a dynamic rule based on a first set of contextual data, or the first set of contextual data includes one or more prior responses to one or more prior alerts by a medical professional. In other cases, the first set of contextual data includes historical data associated with the first patient, or the historical data associated with the first patient includes information regarding the severity level of one or more side effects. In embodiments, an indicator of the alert is displayed. In some cases, the indicator of the alert can be selected by a user.

In some embodiments in accordance with the present invention, a computer-implemented method of alerting users includes receiving an order for a first patient treatment from a first user, determining a potential interaction exists for the order for the first patient treatment, generating a dynamic rule relating to the potential interaction for the order for the first patient treatment, wherein the dynamic rule is based in part on a first set of historical data, and applying the dynamic rule. In some cases, if the system (or a dynamic rule) indicates a first alert should be issued to the first user, the first alert is issued to the first user. In some embodiments, the first set of historical data includes prior interaction data for the first patient. In embodiments, the dynamic rule indicates the first alert should not be issued, because the first set of historical data indicates a second alert, with one or more shared characteristics with the first alert, was overridden. In some cases, the first set of historical data includes prior alert information for the first patient, or the first set of historical data includes prior alert information for the first user. In some examples, the first set of historical data includes prior clinical outcome information for the first patient.

BRIEF DESCRIPTION OF THE DRAWINGS

Embodiments are described in detail below with reference to the attached drawing figures, wherein:

FIG. 3 is an exemplary view of information maintained by an alert response repository module in accordance with embodiments of the present invention;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Figure 1:
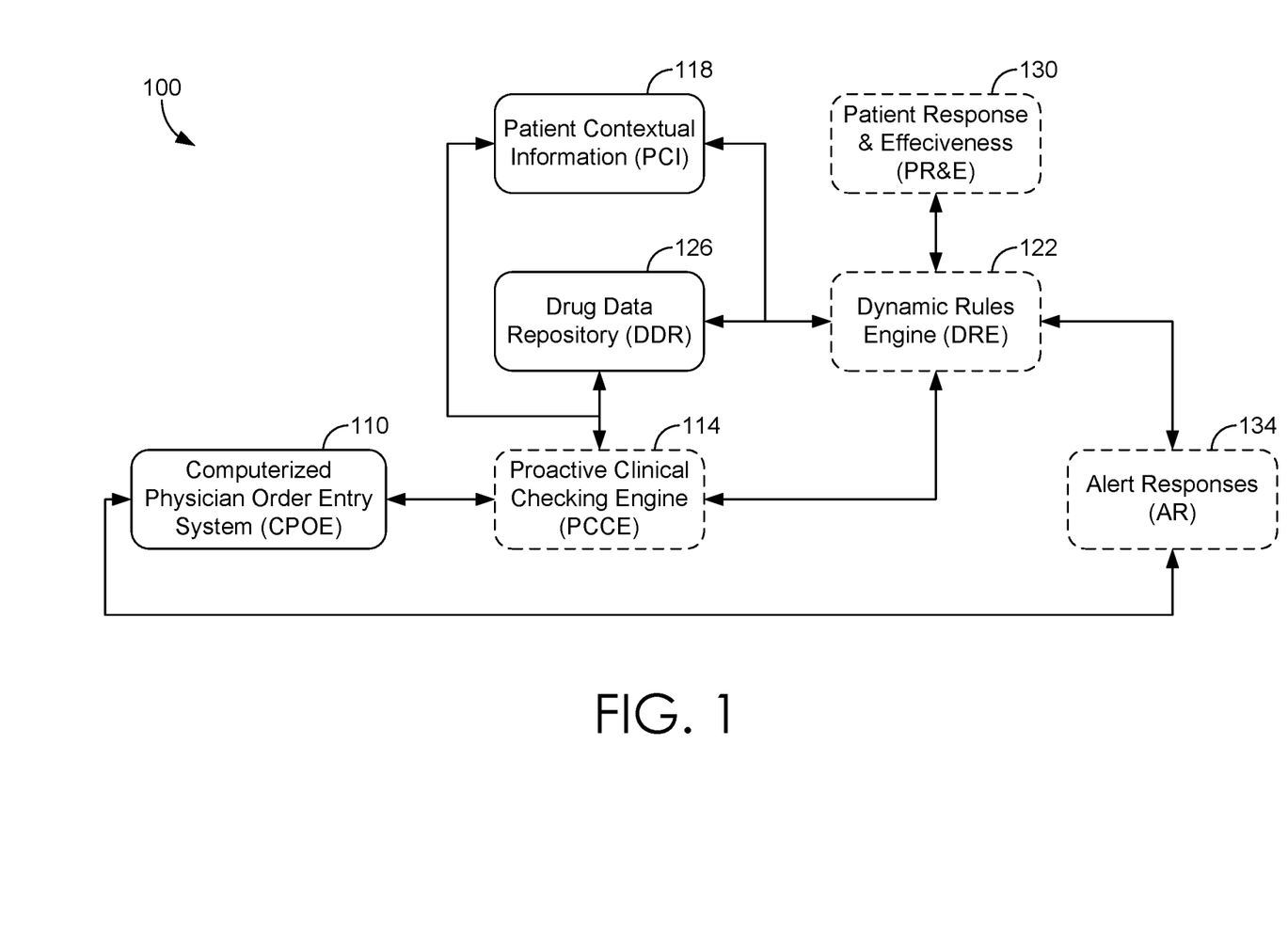
FIG. 1 is a block diagram of an exemplary computing environment suitable to implement embodiments of the present invention.

Embodiments of the present invention are directed to methods, systems, and computer-storage media for performing clinical checking proactively, providing alerts in advance of workflows, and/or reducing alert fatigue. FIG. 1 is an exemplary diagram 100 of computing modules shown as part of a proactive clinical checking system. The modules in FIG. 1 are merely illustrative and additional components, or systems with some or fewer components, can be used to implement a proactive clinical checking system in accordance with embodiments of the present invention. The CPOE module 110 in FIG. 1 is or includes a user interface in embodiments. For example, CPOE module 110 can be a screen, such a touch screen, or a monitor or other display that enables user interaction with the system. Users, such as clinical users, physicians, care providers or others, can interact with the system through CPOE module 110, for example by ordering tests or medications for a patient. In some cases, when a user performs an action such as searching for an order, selecting an order, viewing favorites, pre-configuring orders or order sets, etc., the CPOE module 110 invokes a proactive clinical checking engine (PCCE) 114, discussed in more detail below.

The exemplary embodiment in FIG. 1 includes a patient contextual information (PCI) module 118. PCI module 118 can provide specific information to PCCE 114 and to a dynamic rules engine (DRE) 122, including contextual information. In embodiments, this information is from electronic medical or health records associated with patients. Contextual information can include demographic information and/or clinical characteristics relating to patients. Examples of demographic information are patient age, gender, ethnicity, weight, height, location (such as a geographical tag). Patient clinical characteristics can include, for example, patient allergies, patient problems, diagnosis, current orders relating to a patient (such as medications and lab orders), and patient results.

FIG. 1 also includes a drug data repository (DDR) 126, which can be a database or file that contains or has access to drug and laboratory information, static rules, alternatives, and references. Some examples of DDR 126 include drug databases. A drug database could be, for example, First Databank, National Drug Data File, or another repository. FIG. 1 includes indicators between modules showing communications and flows of information between the exemplary modules in embodiments, for example DDR 126 in communication with PCI module 118, DRE 122, and/or PCCE 114.

As shown in the illustrative components in FIG. 1, a patient response and effectiveness (PR&E) module 130 can be in communication with DRE 122. PR&E module 130 can be a knowledge base or other record of associations between patient responses to prescribed treatments and the effects on clinical outcomes or goals for that patient, discussed in more detail with respect to FIG. 2. Finally, FIG. 1 shows an exemplary alert response (AR) repository 134 in communication with DRE 122 and CPOE module 110. AR repository 134 can maintain information relating to responses to alerts, for example historical information relating to physician responses to alerts. AR repository 134 is discussed in more detail with respect to FIG. 3.

Figure 2:
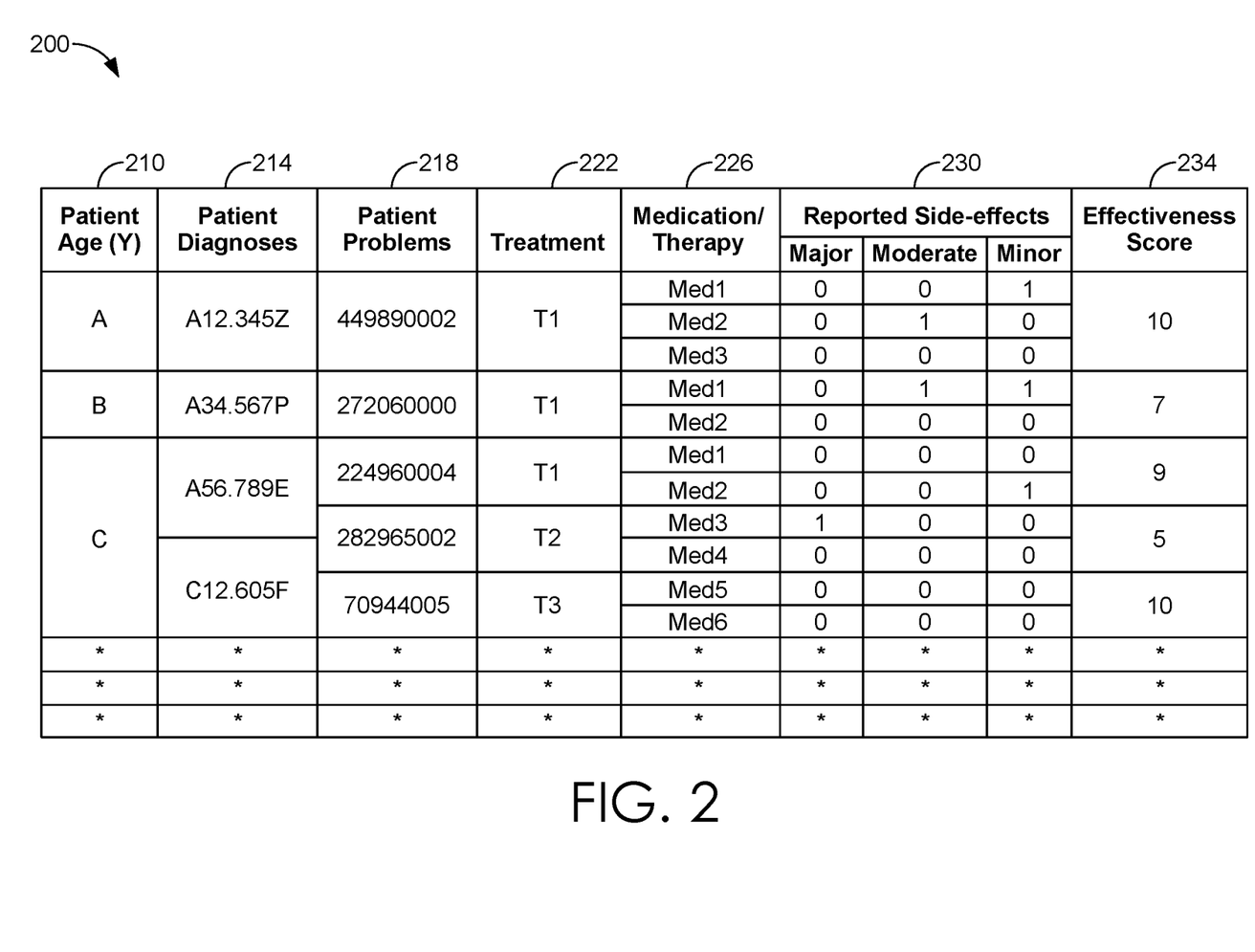
FIG. 2 is an exemplary view of information maintained by a patient response and effectiveness module in accordance with embodiments of the present invention.

Turning to FIG. 2, an exemplary image 200 from PR&E module 130 is shown. The image 200 in FIG. 2 is one example of the types of associations in PR&E module 130. In some cases, PR&E module 130 is a knowledge base that maintains associations. PR&E module 130 may be organized or stored with more or less patient or response associations. In the example in FIG. 2, a patient age column 210 is shown on the far-left side of image 200. FIG. 2 also shows examples of a patient diagnoses column 214, a patient problems column 218, and a treatment column 222. These columns 210, 214, 218, and 222 can contain historical information about patients and treatments. In embodiments, a medication/therapy column 226 shows one or more medications or therapy options used as part of treatment of a patient. As shown in the example in FIG. 2, various combinations of past medications or therapy options in medication/therapy column 226 can be shown for each treatment in treatment column 222. In some cases, a reported side-effects column 230 includes options for major, moderate, or minor side-effects.

On the far-right side of exemplary image 200 in FIG. 2, an effectiveness score column 234 can store effectiveness scores for each treatment in treatment column 222. FIG. 2 shows an effectiveness score in column 234 for each treatment in treatment column 222, but in some cases an effectiveness score could be stored for each medication or therapy shown in medication/therapy column 226. In embodiments, an effectiveness score in column 234 takes into account any reported side effects, but in other embodiments an effectiveness score is separate from any reported side effects. The columns and data image 200 in FIG. 2 are examples; embodiments include more or less associations maintained in PR&E module 130.

FIG. 3 illustrates exemplary information 300 maintained by an AR repository 134. Information 300 is a sample of information that is stored in embodiments, including rows of information such as a first row 314 and a second row 316, and a header row 320 showing the types of information in the first and second rows 314, 316. User column 324 displays a first user (P1) in both first and second rows 314, 316. As shown in the exemplary information 300 in FIG. 3 at 332 (in row 314), the first user (P1) is associated with a first alert for a first medication or therapy (Med1). The medication or therapy associated with the first alert is shown in medication/therapy column 336. Additionally, in this example, the first user (P1) is associated with a second alert in row 316, in association with a second medication or therapy (Med2), as shown at 340. In the embodiment in FIG. 3, an alert category column 344 shows a first alert category 348 for the medication/therapy at 332 (Med1), in this case an alert category of "Drug-Allergy Interaction." Also as shown this embodiment, a second alert category 352 in FIG. 3 is also an alert category of "Drug-Allergy Interaction," in this case in association with the second medication/therapy 340 (Med2). Other alert categories are shown, for example a third alert category 356, in this case a "Drug-Drug Interaction," and a fourth alert category 360, in this case a "Dosage Checking" alert. Any number of medications or therapies, such as first and second medication or therapies 332, 340, can be maintained by AR repository 134. In some cases, several or many rows such as first and second rows 314, 316 are associated with a single user such as a first user (P1).

Alert severity column 364 displays associations maintained by AR repository 134 regarding alert severity for medications or therapies, such as those in medication/therapy column 336. In this example, alert severity column 364 includes a first alert severity 368, for example a first alert severity 368 of "3." A second alert severity 372 is shown in row 316, in this case a second alert severity 372 of "2." These are exemplary values for alert severity. For example, in embodiments, an alert severity of "3" is high, while a "2" is moderate and "1" is low. In other embodiments, other scales, values, or descriptors can be used to indicate alert severity or any other information in the columns shown in the examples in FIGS. 2 and 3. User response column 376 displays information maintained by AR repository 134, including associations of specific, prior alerts with users such as P1, a medication/therapy, an alert category (such as those in alert category column 344), an alert severity, and user responses such as those in user response column 376 in FIG. 3. For example, Med1, as shown at first medication/therapy 332, is associated with a first alert severity 368 of "3" in row 314. In this embodiment, user response column 376 displays a first user response 380 of "A," which can indicate an alert was accepted. Also in this embodiment, user response column 376 shows that AR repository 134 associates a second user response of "O" with a second medication/therapy 340. A response of "O" indicates, in this example, that a first user P1 selected to override an alert associated with Med2 with a second alert severity level 272 of "2." User responses in user response column 376 and other information as shown in the example in FIG. 3 can be stored or organized in other manners, with fewer or more columns, users, severity levels, responses, etc. For example, user response column 376 indicates additional information in some embodiments, such as any follow-up information or steps contributing to a response selected by a medical professional or treating person.

Returning to FIG. 1, the exemplary DRE 122 is a module that creates rules for requests or orders, in embodiments. For example, DRE 122 creates dynamic rules for requests or orders in context, for example by querying contextual information (e.g., from PCI module 118), patient response and effectiveness information (e.g., from PR&E module 130), physician alert responses (e.g., from AR repository 134), and/or drug data repository modules (e.g., from DDR 126). These communications are shown in FIG. 1 in an exemplary embodiment. DRE 122 or another component can receive contextual information from one or more other modules in accordance with embodiments of the present invention.

In some cases, DRE 122 calculates a weighted score for a certain medication or therapy based on a patient's age, for example. Other considerations that can be used to determine a weighted score include a patient's diagnoses, problems, medications, reported side-effects, the effectiveness of the medication, and/or the appropriateness of the medication. Various formulas or calculations can be used to determine a weighted score for a medication or therapy in embodiments. Additionally, a weighted score can be calculated for a combination of medications and/or therapies based on one or more of the same considerations. One example of a calculation and exemplary weights to calculate a score for a medication or therapy is shown below:

$$\begin{aligned}\text{Weighted Score} = &\ (\text{Weight for Patient Age}/100 * \text{Patient Age Match}) + \\ &\ (\text{Weight for Patient Diagnoses}/100 * \text{Number of Diagnoses}) + \\ &\ (\text{Weight for Patient Problems}/100 * \text{Number of Problems/Symptoms}) + \\ &\ (\text{Weight for Medication}/100 * \text{Number of Medications per treatment}) + \\ &\ (\text{Weight for Reported Side-effects}/ \\ &\ (100 * \text{Major value} + 100 * \text{Moderate value} + 100 * \text{Minor value})) + \\ &\ (\text{Weight for Effectiveness score} * \text{Effectiveness value}/1000) + \\ &\ (\text{Weight for Physician Response}/(100 * \text{Response value for Accept} + \\ &\ 100 * \text{Response value for override})) + \\ &\ (\text{Medication Appropriateness Score\#}/100\end{aligned}$$

\#—(Number of ordered occurrences of the medication per given diagnosis/Total number of medications ordered per given diagnosis)

Exemplary Weights

Weight for Patient Age=10%
Weight for Patient Diagnoses=20%
Weight for Patient Problems=15%
Weight for Medication=20%
Weight for Reported Side-effects=10%
Weight for Effectiveness score=10%
Weight for Physician Response=10%
For matched Patient Age=1
If patient age exact match then value=1 else for age range value=5
If Diagnosis exact match, value=1 else for partial match, value=Number of Diagnoses per treatment=3
For Problems exact match, value=1 else for partial match, value=Number of Problems per treatment=2
For Medications exact match, value=1 else for partial match, value=Number of medications per treatment=3
For Major value=0
For Moderate value=0
For Minor value=1
Effectiveness value=10
Override=1 or 0
Accept=2 or 0
If,
Number of ordered occurrences per diagnosis=10
Total number of medications ordered per diagnosis=30
Then,
Medication Appropriateness Score=10/30=0.333
Then, by applying the above formula, $$\begin{aligned}\text{Weighted Score} = &\ (10/100) + (20/100 * 3) + (20/100 * 2) + \\ &\ (20/100 * 3) + (10/100 * (100 * 0 + 100 * 0 + 100 * 1)) + \\ &\ (10 * 10/1000) + (10 * (100 * 0 + 100 * 1)) + (0.333/100) = 0.570\end{aligned}$$

Below are two exemplary rules for illustrative purposes only. In some systems, only static rules are applied, which do not account for patient or medical-professional context. Embodiments of the present invention can include one or more dynamic rules based on a variety of considerations and varying levels of information, for example one or more diagnoses or allergies. The amount of considerations and their values below are only examples. In embodiments, based on the processes information discussed above, for example a weighted score that has been calculated, DRE 122 frames one or more rules for a medication or therapy (such as any medication/therapy listed in medication/therapy column 336 in FIG. 3) that is communicated to PCCE 114, in some cases for additional processing. In embodiments, the rules are informed by how a certain patient at issue (or patients with one or more demographic characteristics in common) responded to the treatment, including the effectiveness of the treatment for a particular diagnosis, side effects, and the severity of side effects. Embodiments of the present invention track and maintain this clinical information and use it later, to target search results before an order for treatment is placed, for example. Below are examples of rules in accordance with embodiments:

Rule 1

For Med x
If patient age is A:
  With,
    Diagnoses: d1, d2, d3
    Problems: p1, p2
    Allergies: a1, a2
    Weighted score: 0.570
  Then,
    Prescribe: Y
  With,
    Drugs: Med x+Med s
    Interactions: Allergy-Drug, Minor
    Alternates: Med c or Med m or Med g+Med p Rule 2

For Med m
If patient is in the age group of A-D:
  With,
    Diagnoses: d1, d3
    Problems: p1, p5, p8
    Weighted score: 0.695
  Then,
    Prescribe: Y
  With,
    Drugs: Med m
    Interactions: None
    Alternates: Med f+Med s or Med u In embodiments, one or more weighted scores are calculated before a clinician or other user has placed an order for any treatment. For example, when a user opens an interface such as CPOE module 110 and indicates, or navigates to a screen relating to, a patient, weighted score for various treatment options can be calculated, in some cases in the background, at this point. The weighted scores indicate the effectiveness or expected effectiveness for certain treatments, in embodiments, and the information used to calculate these weighted scores can be received from stores of information relating to patients, physicians or other users of medical systems, known treatment information (such as literature, studies, demographic-related data for treatments), side effects, etc.

In embodiments of the present invention, the calculation of weighted score(s) for treatments can cause fewer search results (only the effective or most effective) to be displayed when a user begins to enter a search term, as described below. In some cases, this proactive check before an order has even been placed for a patient will conserve time and other resources, because the search results can be targeted to a particular patient, for example. Embodiments allow targeted search results, even based on a few characters that indicate or would have been part of a full search term or phrase, where the system changes the scope of search results based on patient- or physician- (or other caregiver) specific information. For example, if the patient at issue has reported to a medical care facility that a treatment was not working in the past, that treatment can be deemed ineffective for that patient (by its weighted score or other contextual indicators) and removed from the list of potential search results, preventing a medical professional from selecting a treatment a second time that was not effective. In some cases, if a treatment was not effective for a certain age group, condition, or other demographic characteristic, it could be precluded from a search results list. By reducing a list of search results of potential treatments, medical professionals can be more accurate and efficient (and less frustrated or fatigued by unnecessary alerts) and computerized systems can function more efficiently as they are no longer evaluating information that will, ultimately, be deemed not effective for a patient.

An initial set of search results (or any search results prior to placing an order for treatment) can indicate treatments with potential interactions so that a user can select more information on the interaction(s) or avoid placing an order that would be flagged, which saves system resources and avoids additional workflow steps. This indication, as discussed below, can be color-coding or, in some cases, another visual indicator that is readily apparent to the user without additional steps or responses required. In some cases, the dynamic rules can be applied before an order is placed, when a user is viewing or requesting search results (for example based on one or more characters that are a partial search term) so that the most effective treatment is presented at the top of the search results list, or near the top.

The search results displayed prior to an order, such as search results 618 in FIG. 6, discussed below, can warn a user of possible interactions or side effects at the search-order step, before a user has caused the system to accept an order that can trigger other actions, such as pharmacy work or other preparation for treatment (reserving a place for the patient in a certain facility, etc.). This can avoid later alert(s) that require user responses and delay an order for treatment, costing additional medical resources and hindering medical treatment, as well as expending unnecessary system/computational resources. Additionally, a later alert may be reviewed by and acted on by a different medical professional or other user, increasing inconsistencies and chances for error. In embodiments, a user of the system does not have to wait for an order to be placed to receive a warning, including information about interactions, reference materials, etc. Instead, a user can receive a search results list that is targeted to a user based on patient context, or physician context, and avoid ordering treatments that would have later triggered alerts. The search results list can be targeted based on weighted scores as discussed above or other maintained information used to generate dynamic rule(s).

Continuing on with FIG. 1, PCCE 114 can be invoked when a user interacts with a CPOE system to search orders, view orders, make requests, etc., for example based on a medication that is being searched or a list of medications from a preconfigured order set. PCCE 114 can perform clinical checking and, additionally, it can perform dynamic clinical checking as described herein. In embodiments, PCCE 114 communicates with DDR 126 for static rules, and PCCE 114 also invokes DRE 122 for dynamic rules relating to orders or requests in context. PCCE 114 compares the rules and makes a determination in embodiments, and its findings are communicated to a user due to the CPOE system and its inclusion of user interface, in embodiments, discussed in more detail below.

In one example, a weighted score of 0.567 is received for drug amoxicillin, with severe interactions and possible alternatives communicated by DRE 122. In this example, DDR 126 indicates there would be a severe interaction with drug methotrexate, which is indicated as already present in the patient's medication list. In this example, PCCE 114 would communicate to or using the CPOE that the drug amoxicillin is not an appropriate drug to be prescribed for the patient with the current context and suggests alternatives for the drug amoxicillin, based on information maintained or accessed by one or more modules in or connected to the CPOE. As the value of a weighted score moves closer to "1," the appropriateness of the drug increases, for example. Other scales or indicators of the appropriateness or danger of a medication or therapy may be used in embodiments of the present invention.

In some embodiments, the information or results generated by DRE 122 may contradict information from DDR 126. For example, a weighted score may be closer to a value of "1" for a particular medication or therapy (indicating it is effective), but a patient may suffer side-effects in association with that medication. In this case, embodiments of the present invention provide suggestions for additional one or more medications or therapies to be prescribed in combination with the particular medication or therapy at issue, in order to treat anticipated side-effects or interactions, for example based on allergy-drug interaction information maintained or accessed by embodiments of the present invention.

A clinical checking process, in some cases, is phased into more than one stage. The stages can depend on the availability of information relating to an order or request (such as an order or request input to a CPOE 110 by a user such as a physician (P1)) and patient-specific information. Multiple stages can serve various purposes or provide flexibility to a system, and in some cases can aid in proactive alerts or suggestions to users of possible interactions.

Figure 4:
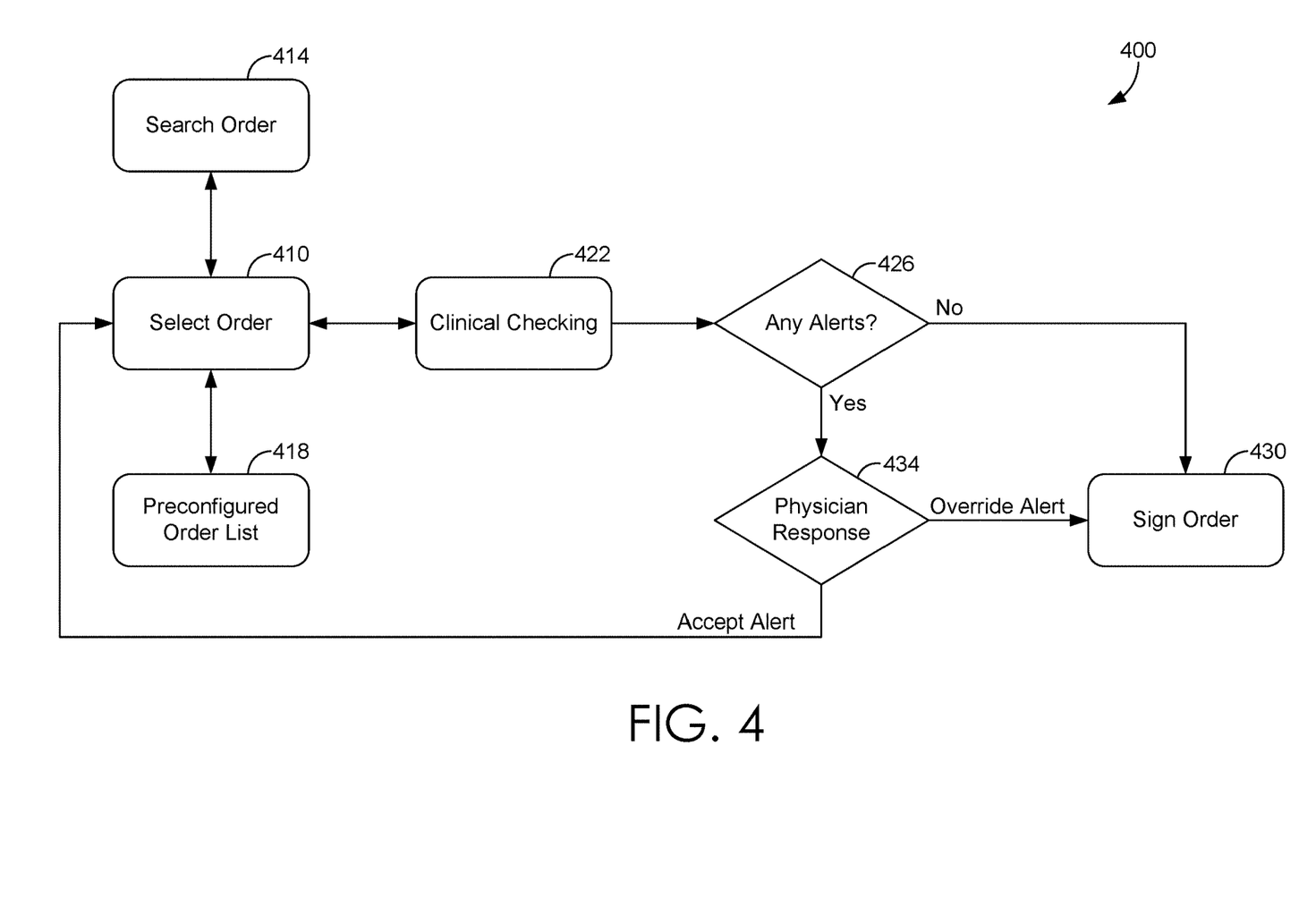
FIG. 4 is a flow diagram of an exemplary method of determining and responding to potential alerts based on clinical checking.

FIG. 4 includes a flow diagram 400 relating to a non-enhanced or non-proactive system. The system or module in FIG. 4 enables users such as care providers and physicians to (1) search for required therapies or tests and/or medications, or (2) choose from a preconfigured list of therapies or tests and/or medications. As shown in FIG. 4, a select order step 410 receives information relating to an order (at search order 414) and/or relating to a list (at preconfigured order list 418). Based on an order as shown at select order step 410, clinical checking step 422 can contribute to determining if any alerts exist, as shown at alert determination step 426. If no alerts exist, a user such as a physician can approve a therapy, test, and/or medication, as shown at sign order step 430. If an alert is determined or communicated, a user responds to an alert, as shown by physician response step 434. The user can respond by, for example, overriding the alert, which can result in sign order step 430 as shown in FIG. 4. The user can respond by, in another example, accepting the alert, in which case the user may be returned to the select order step 410. The non-enhanced or non-proactive system shown in the example in FIG. 4 can lead to alert fatigue in some cases, if alerts are not eliminated or suppressed as described herein in relation to embodiments, for example because contextual information is not received and/or because a proactive clinical checking engine (such as PCCE 114) is not implemented. As shown in FIG. 1, in embodiments of the present invention, various modules, such as PCCE 114, PCI module 118, PR&E 130, and/or AR repository 134, can inform DRE 122 and communicate in return with PCCE 114 and CPOE 110 (at one or more points in time including at various stages of a clinical checking process).

Figure 5:
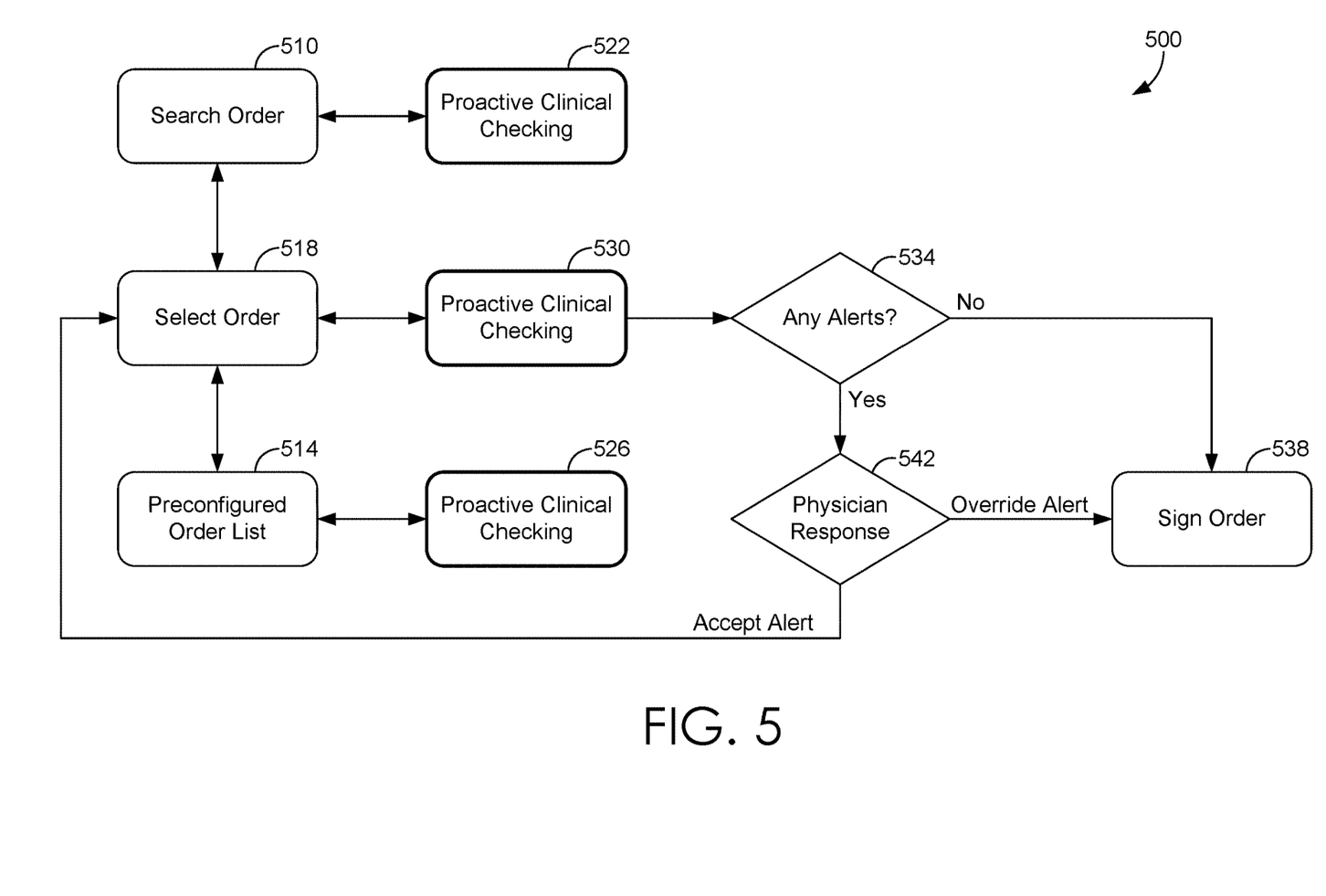
FIG. 5 is a flow diagram of an exemplary method of determining and responding to potential alerts based a proactive clinical checking in accordance with embodiments of the present invention.

Turning to FIG. 5, an exemplary flow diagram 500 of a process employing one more PCCE 114 modules is shown. In some examples, a clinical checking process is divided into two stages or two main stages. Stage one includes pre-order selection clinical checking, for example, which can include one or more searches or search lists and one or more preconfigured lists. Steps relating to this stage are shown at search order step 510 and preconfigured order list step 514 in FIG. 5. A second stage, in this example, includes post-order selection clinical checking, which occurs after a search order step 518. As shown in the embodiment of the present invention in FIG. 5, a first proactive clinical checking step 522 occurs in relation to search order step 510, and a second proactive clinical checking step 526 occurs in relation to preconfigured order list step 514. These proactive clinical checking steps 522, 526 are part of a first stage, in one example. A third proactive clinical checking step 530 can occur in relation to search order step 518 (and/or be post-order), in this example, thereby being part of a second stage. The proactive clinical checking steps, at any stage or in relation to any step, can invoke PCCE 114 as shown in FIG. 1 and/or DRE 122 as shown in FIG. 1, in embodiments. In other embodiments, proactive clinical checking steps as shown in FIG. 5 can invoke AR repository 134, PCI module 118, and/or PR&E 130, in embodiments.

At alert step 534 in the exemplary process in FIG. 5, a system determines if any alerts exist to be communicated or displayed to a user, such as a health care worker. If no alerts exist, a user may approve a test, therapy, or medication order as shown at sign order step 538, in embodiments. In some cases, if one or more alerts exist and are communicated or displayed to a user, a user may respond to the alert, for example as shown at physician response step 542. A user, for example the health care worker or other caregiver, can select to override the one or more alerts, resulting in sign order step 538, for example. Or a user can accept on or more alerts, which in some cases can in returning to select order step 518 (or returning to search order step 510 and/or preconfigure order list step 514, as a return to stage one, for example). A system may return a user to stage one after accepting one or more alerts if additional information may be available to inform an analysis at stage one.

In embodiments of the present invention, a second stage of clinical checking occurs. Examples of checks performed during stage two include, in some cases, a dose range check, a check for drug-drug interactions (using selected orders and a current medication order list), and/or an IV compatibility check. When a user such as a caregiver or physician selects the order(s) they want to place for a patient (including medications, therapies, or tests), PCCE 114 is invoked. An output is communicated back to a CPOE system, such as CPOE module 110, as shown in the illustrative environment in FIG. 1.

In one example, a user navigates to or opens CPOE module 110, causing the system to execute a first stage of clinical checking by invoking PCCE 114 in the background. Other user actions can cause a first stage of clinical checking to be activated by the system. For example, as shown in FIG. 5, search order step 510 and/or preconfigured order list step 514 can occur (in some cases in the background) when a select order step 518 begins, or when a user opens or goes to CPOE module 110 but before a search order step 518 has commenced. In some cases, a user causes background, stage one clinical checking by accessing any portion of an interface to reach select order step 518 or CPOE module 110, or when a threshold of patient or user information has been received by CPOE module 110 or during the select order step 518. In some embodiments, CPOE module 110 includes a user interface and accessing the user interface causes a first stage of checking including pre-checks in the background. As shown in FIG. 5, search order step 510 and/or preconfigured order list step 514 can include proactive clinical checking steps 522, 526 as part of stage one, as well. In some cases, when a user such as a caregiver navigates to a preconfigured list, for example as in preconfigured order list step 514, a PCCE process by PCCE 114 is executed.

In another example, if a user searches for an order at select order step 518, such as by entering text in a search box as discussed below, PCCE 114 begins one or more PCCE processes that are executed on the search results for the user's search. In this example, search results are presented to the user in a manner that differentiates between orders (such as therapies, medications, or tests) that have potential or definite interactions and those without interactions, for example by formatting text differently for orders with and without interactions determined by the system. A response including search results received from PCCE 114 can indicate interactions and their associated severity levels, in embodiments, which aids the user in identifying all orders with interactions in order to refrain from ordering those items and/or to select one or more alternatives, in some cases as suggested by the system.

The following is one specific example. A male patient, age 45, has arthritis problems. The patient is already on a medication, methotrexate. The patient visited a medical professional, for example a physician, and complained about abdominal pain. The physician can examine the patient and order tests, after which the patient is diagnosed with a bladder infection. In this example, the physician intends to prescribe a course of amoxicillin capsules for approximately five days. In this example, the intended prescription (amoxicillin) interacts severely with methotrexate. In a non-enhanced or non-proactive clinical checking system, the physician submits an order for amoxicillin, and the system displays an alert for possible interactions. The physician must respond to the alert to complete the ordering process by changing the medication or overriding the alert (if allowed by an organization's policies).

In a proactive clinical checking system, a pre-check is performed by invoking a PCCE 114 module before an order is placed by the physician. This pre-check provides visual indicators through CPOE module 110 which can be or include an interface (or through another display or interface associated with the clinical checking system). The visual indicators associated with the pre-check (for example checks at search order step 510 and/or at preconfigured order list step 514, performed before a select order step 518, in embodiments) indicate possible interactions, which can aid the physician to make an intelligent or informed decision when first placing an order, for example at select order step 518.

A check can be caused by a caregiver or physician searching for an order, such as a medication, therapy, or test, for example at search order step 510. A check can also be caused by a user viewing preconfigured orders or lists, for example at preconfigured order list step 514 as shown in FIG. 5. A pre-check or check at the first stage, before an order has been selected at select order step 518, can include, in embodiments: a drug-allergy check, using patient allergy information, for example; drug-drug interactions, using patient current-medication list(s), for example; drug-food checking, using documented patient food habits or from an organization's food/diet management systems; duplicate therapy check, using patient current-order list(s); and/or ABN (Advanced Beneficiary Notification) checking or necessity check, using charted diagnoses. Results from a pre-check or other checks performed during a first stage are communicated to CPOE module 110 in embodiments, which provides or causes user-interface communications to users such as physicians.

In embodiments in accordance with the present invention, one or more alerts are suppressed by the system, in some cases in response to a dynamic rule. For example, information from PCI module 118, PR&E 130, and/or AR repository 134 can be used alone or in combination to cause a rule that suppresses one or more alerts. In an embodiment, a certain physician or caregiver has historical data associated with them indicating one or more alerts have been overridden or ignored in past situations, which may have one or more characteristics in common with the current patient's situation. In an example, a certain physician's prior responses to alerts causes a dynamic rule for a certain user or patient that suppresses one or more alerts, because they are likely to cause alert fatigue and unlikely to cause an update to an order. In some cases, data from multiple physicians or caregivers (instead of the current user) is considered and contributes to a dynamic rule that causes an alert to be suppressed. In other cases, historical data regarding a patient or stored information about patient reactions can be used to determine that an alert should be suppressed, for example if the same or a similar alert has been suppressed in the past (and, in some cases, a threshold of changes in information or circumstances has not been met). In these cases, the data maintained or accessed by components of the system can determine when it would be more effective to suppress one or more alerts in order to improve efficiency and patient care. An alert that has been suppressed can still be displayed or indicated so that a user can select to receive more information, even though the alert may not require a user response do to the suppression of the alert.

Figure 6:
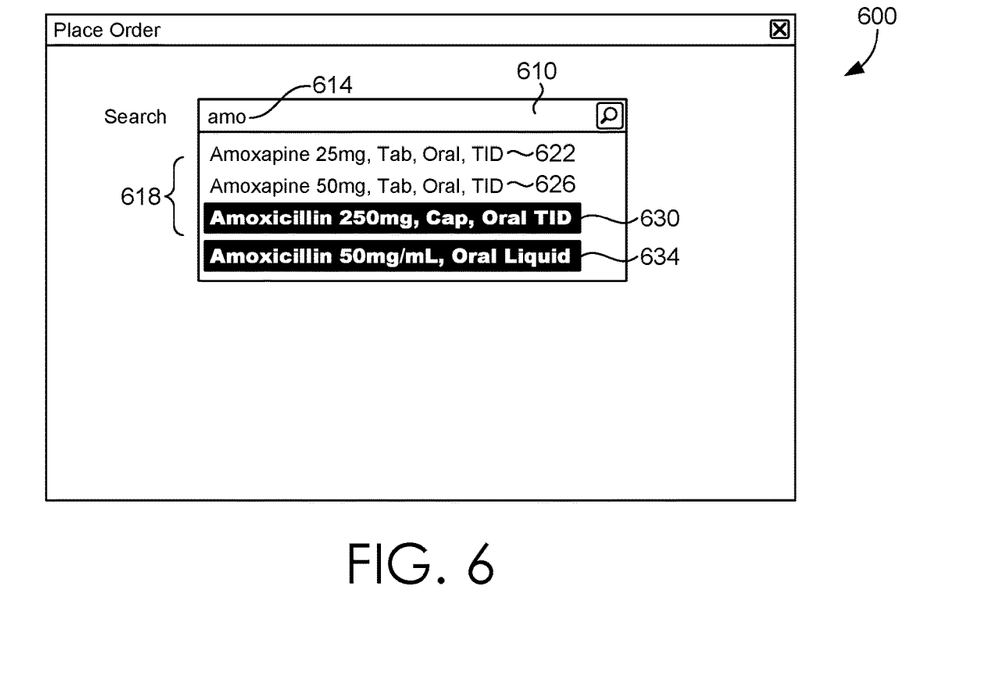
FIG. 6 is an exemplary graphical user interface illustrating information presented during a place order process or step in accordance with an embodiment of the present invention.
Figure 7:
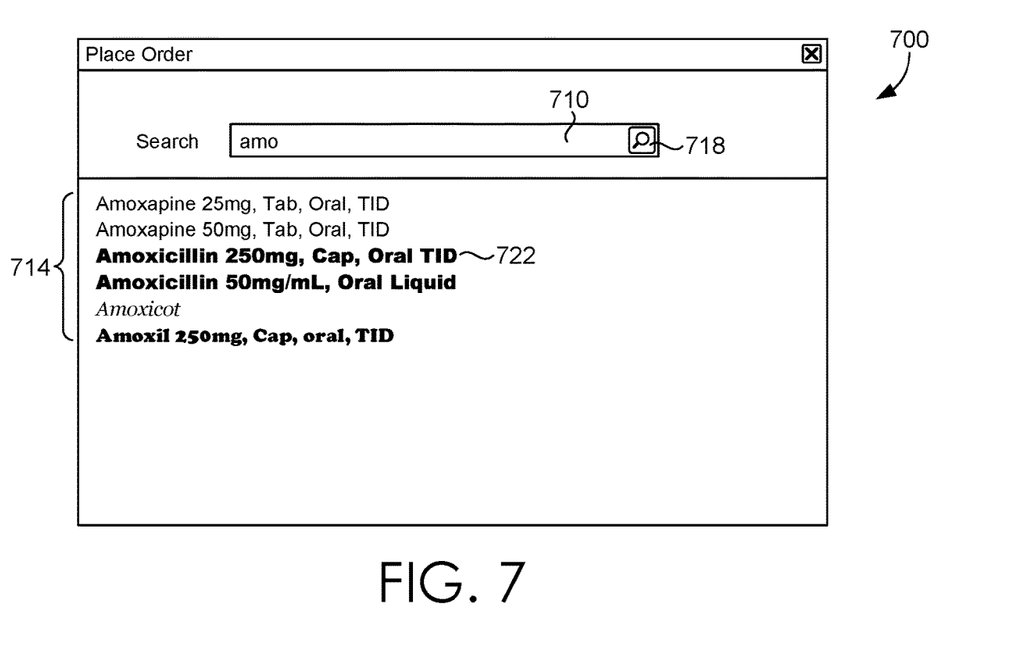
FIG. 7 is an exemplary graphical user interface illustrating information presented during a place order process or step in accordance with an embodiment of the present invention.
Figure 8:
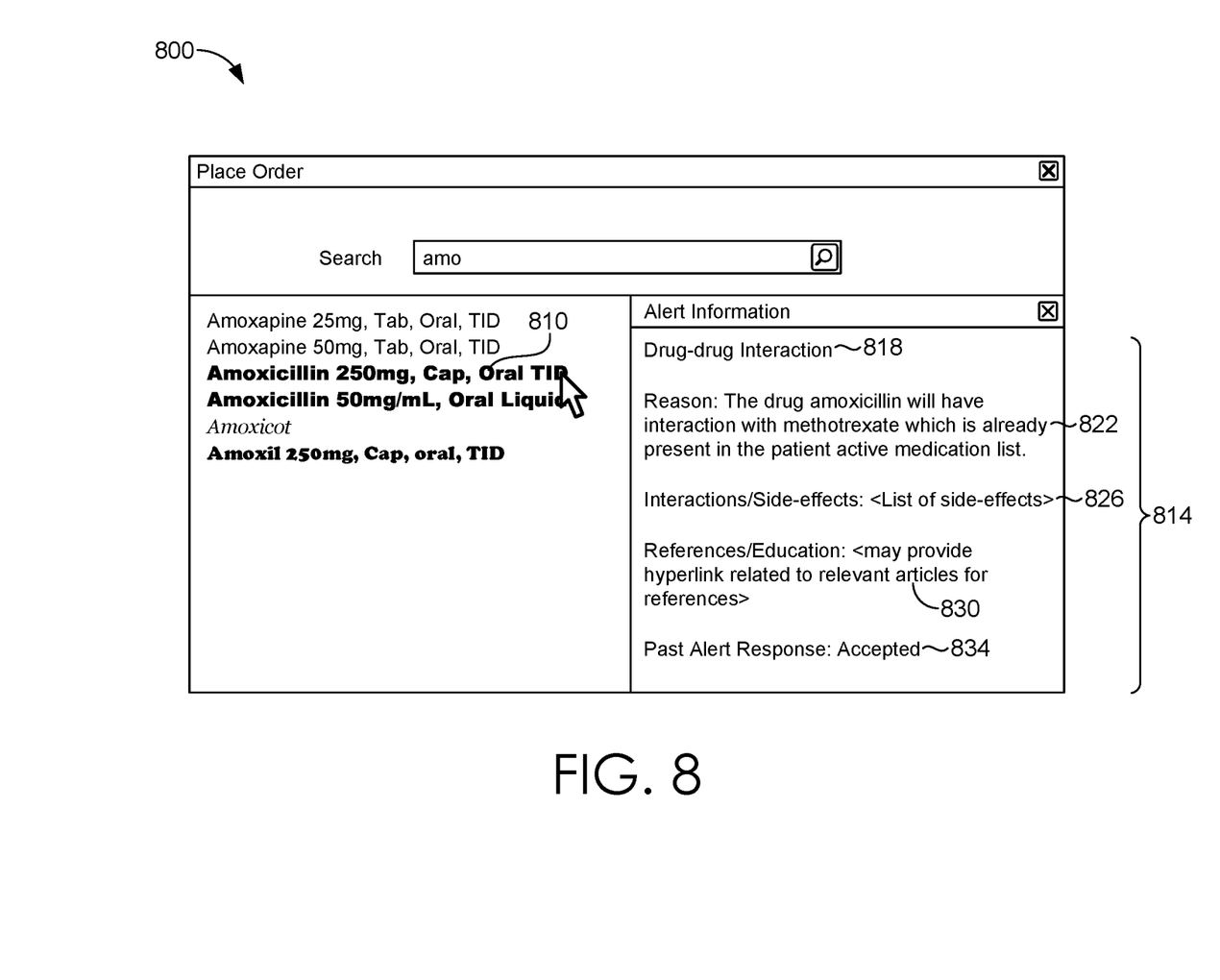
FIG. 8 is an exemplary graphical user interface illustrating information presented during a place order process or step in accordance with an embodiment of the present invention.

FIGS. 6-8 are exemplary user-interfaces. These examples are for illustration purposes only. Embodiments of the present inventions can include various aspects of user-interfaces in addition to, or instead of, the user-interface examples shown here. The various user interfaces in embodiments of the present invention can be displayed to a user by CPOE module 110 or another interface associated with the system, in embodiments. In some cases, the exemplary interfaces and other embodiments as represented by FIGS. 6-8 include graphical user interfaces.

FIG. 6 illustrates a user-interface display 600 for searching an order, for example a search order step 518 as shown in FIG. 5. Display 600 includes search box 610, where a user such as a physician can begin entering or typing information in order to begin a search order step 518. As shown in the example in FIG. 6, a user enters one or more characters into search box 610, such as search term (or partial search term) "amo" as shown at 614. In this example, the search term "amo" shown at 614 generates a search results list 618 with, in this case, four results. The first two results 622, 626 in search results list 618 (both for dosage levels of "Amoxopine") are displayed in plain text as shown in FIG. 6. The third and fourth results 630, 634 in search results list 618 are both for dosage levels of "Amoxicillin."

The third and fourth search results 630, 634 are shown in search results list 618 as being highlighted, because a pre-check indicates interactions would be expected for these two search results. In some cases, these two search results 630, 634 could be bolded or marked or written in another color. In embodiments, other indicators are used to flag or highlight the search results where interactions are expected. As shown in FIG. 6, a user would receive interaction information (e.g., highlighting in color of the two options with interactions) prior to ordering a medication, therapy, or test. In this example, the physician has not placed an order (e.g., as shown at place order step 518). Therefore, the physician does not have to wait for an alert to be determined after an order is placed, at which point the physician would have to change or update an order or override an alert (or re-do placing an order). Instead, in embodiments of the present invention, an interaction check occurred in the background of the system in order to flag the third and fourth search results 630, 634 before an order is placed.

Turning to FIG. 7, an image 700 of search order results is shown based on, for example, a search order step 510 as shown in FIG. 5. Search box 710 in FIG. 7 shows a search has begun or been executed for "amo." A search results list 714 is shown with six results, which can be displayed in image 700 when a user such as a caregiver hits enter, select, or a search icon such as icon 718 in FIG. 7. In embodiments, one or more colors of text or highlighting can be used to differentiate the search results based on interactions. For example, both "Amoxicillin" search results in search results list 714 in FIG. 7 could be in red text, because they are determined to have interactions with a patient's existing medication(s).

Search result 722 in FIG. 7, which in this example is shown with text reading "Amoxicillin 250 mg, Cap, Oral TID," is displayed in red text to indicate one or more interactions determined before an order for medication, therapy, or tests has occurred. In embodiments, the use of one or more color-coded texts in search result list 714 corresponds to and indicates one or more alerts, which can have one or more severity levels. A user can click on or hover over a search result, such as search result 722, to receive or view a display of additional alert information.

FIG. 8 shows an exemplary display 800 that a user views, in some cases when a user has selected a search result (e.g., search result 810), including an example of an alert information panel 814. For example, alert information panel 814 is displayed in some cases when a search result 810 is selected by a user. A panel or display of alert information can include details of interactions and past physician responses to similar alerts or conditions. In embodiments, an alert information panel 814 includes one or more of a category or type of interaction 818; one or more reasons for the interaction(s) 822; side effects 826; reference materials related to the interaction(s) that can be accessed 830; and prior responses 834 by users such as physicians, caregivers, etc. In some cases, only physician responses are included or considered in developing rules in accordance with embodiments of the present invention, to the exclusion of other users such as caregivers. In some cases, on or more types of medical professionals are included in the records maintained of historical responses that can be displayed or relied upon to, for example, suppress alert(s).

The following is one specific example intended to illustrate an instance of an embodiment of the invention. In this example, a physician intends to prescribe amoxicillin for pain for a first patient. The physician (a user of the system) would search for amoxicillin in a search box in a CPOE user interface. The search operation would invoke PCCE 114 module, which can communicate with DDR 126 for any interactions involving an amoxicillin drug with one or more drugs on a patient medication list. In this example, because the patient is already taking methotrexate for arthritis problems, DDR 126 would provide an interaction indicator for methotrexate. PCCE 114 also, in embodiments, invokes DRE 122 to generate one or more dynamic rules associated with amoxicillin. DRE 126 can generate dynamic rule(s) based, for example, on data available in the system and/or using formula to generate a weighted score for the medication, where a score closer to value of "1" would represent the most appropriateness of the medication for the given context. PCCE 114 can receive rule(s) from DRE 126 and analyze the same along with the information from DDR 126, in embodiments. If both the rule(s) and the information from DDR 126 have similar outcomes or implications, say for instance the interactions are the same or similar, PCCE 114 sends appropriate response information indicating the interactions to CPOE module 110, which can handle or present the information through a user interface, for example the exemplary interfaces shown in FIGS. 6-8.

In one example, a recommendation based on rule(s) and information is to not issue a prescription for a medication, PCCE 114 sends appropriate information alerting against or otherwise indicating not to issue a prescription, to CPOE module 110. This information can be provided before an order is placed, for example at select order step 518 in FIG. 5, in order to eliminate alerts, including later alerts during a more advanced point in the workflow that may require going back, changing or updating or cancelling an order, or that may risk being ignored due to the frequency or volume of alerts. Embodiments of the present invention enable alerts (or flagging of potential orders) to be displayed on an interface to a user prior to an order being selected, in some cases, for example with red text for search results that have interactions indicated and access to more information prior to an order selection. This pre-check procedure provides visual information at the earliest point in the workflow in a proactive manner, which enables users to avoid later alerts and alert fatigue, as discussed below.

In other cases, one or more rules may indicate that the specific interaction at issue has been overridden in the past, or is not severe, or some combination of this information, in order to suppress an alert of flagging related to a potential treatment option. In some cases, a consideration may be the effectiveness of a medication, therapy, or test versus interactions, side-effects, and the severity levels of one or both, alone or in combination with the considerations directly above. Dynamic rules from DRE 126 based on historical information, alert treatments, and other context, can eliminate excessive alerts that will likely (or almost certainly) be ignored or overridden. This suppression of alerts can occur at any stage or point in a workflow. In embodiments, the later alerts that occur after ordering are suppressed (when appropriate based on context and rules) in favor of pre-check indications through a user interface based on proactive, background analysis—for example the flagged or color-coded search results that link to additional information (including alert information panel 814) prior to an order placement and/or during the placement of an order, before it is completed. As shown in FIG. 5, for example, contextual information is received and/or a proactive clinical checking engine (such as PCCE 114) is implemented at one or more steps, in a first stage including as part of a pre-check and/or in a second stage. PCCE 114 receives or considers information relating to, for example, context such as expected versus actual outcomes (for a specific patient, medical institution, or more generally based on reference material(s)), specific side effects for a patient or demographic or in general, and other information available to the system.

Embodiments of the present invention generate or implement dynamic, proactive clinical checking, which can aid users in ordering the appropriate and effective therapies and medications for patients based on the patient themselves and additional context, thereby providing better patient care and/or clinical outcomes with less risk of alert fatigue, for example. Embodiments of the system and methods herein provide proactive alerts at earlier points of the workflow (before an order selection, for example), which mitigates against alert fatigue in caregivers, physicians, etc. This can provide a safer clinical environment and more effective patient care. The changes in alerts within workflows as described with respect to embodiments of the present invention improve physician treatment, for example, by alerting the physician during a first stage before an order has been placed with a proactive alert. This can also reduce costs for medical institutions such as hospitals, including reducing readmissions or revisits and reducing unnecessary workflow interruptions due to non-priority alerts, which could be resolved based on context or other information by embodiments of the present invention. In some cases, a higher level of quality of care can lead to incentives, including financial incentives and government incentives, for medical organizations or physicians.

Embodiments of the present invention can cause, for example, the user interface to show search results that are targeted to a user or patient, by eliminating treatment options in some cases, placing certain treatments at the top of a list, and providing one or more indicators of possible interactions at the search result stage. The user interface can provide this information (before an order is placed) based on, for example, a pre-check that considers patient contextual information or user contextual information (e.g., prior overrides of alerts by a user, or by users at the same medical facility, or by users treating patients with the same diagnosis, or, for example, users treating patients with the same diagnosis where the patients are also the same gender, age group, living in a similar location, etc.). Embodiments of the system described herein provide contextual search results, so that a user does not have to scroll or navigate to additional pages to review the pertinent results, and they provide treatment predictions based on contextual information. Embodiments therefore can eliminate interruptions to a workflow, and eliminate the need to backtrack from an existing, placed order back to the place-order step (which, after the time required, can cause errors that would not have occurred in the absence of backtracking later).

Embodiments provide tailored search results with an ability to see indicators of alerts and view additional information, instead of being forced to respond to an alert. This option prevents users from simply overriding alerts in order to keep working or accessing the system. For example, if interaction information is available and a search result is color-coded to indicate an interaction, a user can consider this interaction before making any selections that would have to be undone. In some cases, embodiments provide search results to a user that are appropriate for the specific patient (based on patient history, for example), not just for the patient's age group. For example, the effectiveness score for a treatment can determine if the treatment is listed as search result or not, or where in the list of search results it will appear. In some cases, the effectiveness score for a treatment or its warnings are based on the specific patient, but it some cases they are based on data for the patient's age group or specific diagnosis, for example.

The exemplary modules in diagram 100 and discussed herein are suitable for use in implementing embodiments of the present invention. The modules are merely an example of one suitable computing system environment and are not intended to suggest any limitation as to the scope of use or functionality of embodiments of the present invention. Neither should the computing system environment be interpreted as having any dependency or requirement related to any single module/component or combination of modules/components illustrated therein. Embodiments of the present invention might be operational with numerous other computing system environments or configurations. Examples of computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computer-implemented method for proactively reducing electronic alert issuances through real-time dynamic rule creation that is integrated into a computerized search function, the method comprising:

receiving, by a proactive clinical checking engine integrated with a computerized physician order entry system, a string of characters being input by a user as a query;

determining the string corresponds to one or more medical treatments concurrent with receiving the string of characters being input by the user as the query;

in response to determining that the string of characters being input corresponds to the one or more medical treatments, determining, by a drug data repository in near real-time, that a potential interaction exists for at least a first medical treatment in the one or more medical treatments for a particular patient;

in response to determining the potential interaction exists, creating, by a dynamic rules engine in near real-time, a dynamic suppression determination rule, wherein the dynamic suppression determination rule relates to the potential interaction for the first medical treatment, wherein creating the dynamic suppression determination rule comprises:

querying a first set of historical data that includes one or more demographic characteristics of the particular patient and one or more effectiveness scores for each of the one or more medical treatments for the particular patient; and calculating weighted scores for each of the one or more medical treatments including the first medical treatment being determined concurrent with receiving the string of characters being input by the user as the query, wherein the weighted scores are calculated based on the one or more demographic characteristics and the one or more effectiveness scores;

applying, by the proactive clinical checking engine in near real-time, the dynamic suppression determination rule to identify a first set of search results for the string of characters being input, wherein the first set of search results includes a subset of the one or more medical treatments, and wherein the first set of search results are identified for the particular patient based on the weighted scores; and causing display, via the computerized physician order entry system and concurrent with the string of characters being input by the user, of the first set of search results in a ranked order that based on the weighted scores for the subset of the one or more medical treatments in a graphical user interface, wherein the first set of search results does not include the first medical treatment as suppressed by the dynamic suppression determination rule based on the potential interaction to prevent selection of the first medical treatment, and wherein the first set of search results are selectable by the user in the graphical user interface.

2. The method of claim 1, wherein the first set of historical data includes prior clinical information for the particular patient.

3. The method of claim 1, wherein the first set of historical data includes prior information for the user.

4. The method of claim 1, wherein the dynamic suppression determination rule indicates the first medical treatment is not to be displayed as the first medical treatment was not effective for the particular patient based at least on the first set of historical data.

5. The method of claim 1, wherein the first set of historical data includes data relating to one or more other patients that share one or more demographic characteristics with the particular patient.

6. The method of claim 1, wherein the weighted scores are calculated by summing two or more of:
   (a weight for patient age/100×a patient age match);
   (a weight for patient diagnoses/100×a quantity of diagnoses);
   (a weight for patient problems/100×a quantity of problems); or
   (a weight for medication/100×a quantity of medication(s) per treatment).

7. The method of claim 6, wherein the weighted scores are further calculated by additionally summing one or more of:
   (a weight for a reported side effect/(100×a major value+100×a moderate value+10×a minor value));
   (a weight for an effectiveness score×an effectiveness value/1000);
   (a weight for a physician response/(100×an accept response value+100×an override response value)); or
   ((a medication appropriateness score/100)−(a quantity of ordered occurrences of a medication per a particular diagnosis/a total quantity of medications ordered per that particular diagnosis)).

8. A computing system comprising:
   at least one processor connected to at least one memory;
   computer-storage media comprising computer-executable instructions stored thereon, wherein the computer-executable instructions are configured to implement a computerized physician order entry system that when executed by the at least one processor, cause the processor to perform functions comprising:
   receiving, by a proactive clinical checking engine integrated with the computerized physician order entry system, a string of characters being input by a user as a query;
   determining the string corresponds to one or more medical treatments concurrent with receiving the string of characters being input by the user as the query;
   in response to determining that the string of characters being input corresponds to the one or more medical treatments, determining, by a drug data repository in near real-time, that a potential interaction exists for at least a first medical treatment in the one or more medical treatments for a particular patient;
   in response to determining the potential interaction exists, creating, by a dynamic rules engine in near real-time, a dynamic suppression determination rule, wherein the dynamic suppression determination rule relates to the potential interaction for the first medical treatment, wherein creating the dynamic suppression determination rule comprises:
      querying a first set of historical data that includes one or more demographic characteristics of the particular patient and one or more effectiveness scores for each of the one or more medical treatments for the particular patient; and
      calculating weighted scores for each of the one or more medical treatments including the first medical treatment being determined concurrent with receiving the string of characters being input by the user as the query, wherein the weighted scores are calculated based on the one or more demographic characteristics and the one or more effectiveness scores;
   applying, by the proactive clinical checking engine in near real-time, the dynamic suppression determination rule to identify a first set of search results for the string of characters being input, wherein the first set of search results includes a subset of the one or more medical treatments, and wherein the first set of search results are identified for the particular patient based on the weighted scores; and
   causing display, via the computerized physician order entry system and concurrent with the string of characters being input by the user, of the first set of search results in a ranked order that based on the weighted scores for the subset of the one or more medical treatments in a graphical user interface, wherein the first set of search results does not include the first medical treatment as suppressed by the dynamic suppression determination rule based on the potential interaction to prevent selection of the first medical treatment, and wherein the first set of search results are selectable by the user in the graphical user interface.

9. The computing system of claim 8, wherein the first set of historical data includes prior clinical information for the particular patient.

10. The computing system of claim 8, wherein the first set of historical data includes prior information for the user.

11. The computing system of claim 8, wherein the dynamic suppression determination rule is configured to indicate that the first medical treatment is not to be displayed as the first medical treatment was not effective for the particular patient based at least on the first set of historical data.

12. The computing system of claim 8, wherein the first set of historical data includes data relating to one or more other patients that share one or more demographic characteristics with the particular patient.

13. The computing system of claim 8, wherein the computer-executable instructions are configured to calculate the weighted scores by summing two or more of:
(a weight for patient age/100×a patient age match);
(a weight for patient diagnoses/100×a quantity of diagnoses);
(a weight for patient problems/100×a quantity of problems); or
(a weight for medication/100×a quantity of medication(s) per treatment).

14. A computer-storage media comprising computer-executable instructions stored thereon, wherein the computer-executable instructions are configured to implement a computerized physician order entry system that when executed by at least one processor of a computing system, cause the computing system to perform functions comprising:
receiving, by a proactive clinical checking engine integrated with the computerized physician order entry system, a string of characters being input by a user as a query;
determining the string corresponds to one or more medical treatments concurrent with receiving the string of characters being input by the user as the query;
in response to determining that the string of characters being input corresponds to the one or more medical treatments, determining, by a drug data repository in near real-time, that a potential interaction exists for at least a first medical treatment in the one or more medical treatments for a particular patient;
in response to determining the potential interaction exists, creating, by a dynamic rules engine in near real-time, a dynamic suppression determination rule, wherein the dynamic suppression determination rule relates to the potential interaction for the first medical treatment, wherein creating the dynamic suppression determination rule comprises:
querying a first set of historical data that includes one or more demographic characteristics of the particular patient and one or more effectiveness scores for each of the one or more medical treatments for the particular patient; and
calculating weighted scores for each of the one or more medical treatments including the first medical treatment being determined concurrent with receiving the string of characters being input by the user as the query, wherein the weighted scores are calculated based on the one or more demographic characteristics and the one or more effectiveness scores;
applying, by the proactive clinical checking engine in near real-time, the dynamic suppression determination rule to identify a first set of search results for the string of characters being input, wherein the first set of search results includes a subset of the one or more medical treatments, and wherein the first set of search results are identified for the particular patient based on the weighted scores; and
causing display, via the computerized physician order entry system and concurrent with the string of characters being input by the user, of the first set of search results in a ranked order that based on the weighted scores for the subset of the one or more medical treatments in a graphical user interface, wherein the first set of search results does not include the first medical treatment as suppressed by the dynamic suppression determination rule based on the potential interaction to prevent selection of the first medical treatment, and wherein the first set of search results are selectable by the user in the graphical user interface.

15. The computer-storage media of claim 14, wherein the first set of historical data includes prior clinical information for the particular patient.

16. The computer-storage media of claim 14, wherein the first set of historical data includes prior information for the user.

17. The computer-storage media of claim 14, wherein the dynamic suppression determination rule is configured to indicate that the first medical treatment is not to be displayed as the first medical treatment was not effective for the particular patient based at least on the first set of historical data.

18. The computer-storage media of claim 14, wherein the first set of historical data includes data relating to one or more other patients that share one or more demographic characteristics with the particular patient.

19. The computer-storage media of claim 14, wherein the computer-executable instructions are configured to calculate the weighted scores by summing two or more of:
(a weight for patient age/100×a patient age match);
(a weight for patient diagnoses/100×a quantity of diagnoses);
(a weight for patient problems/100×a quantity of problems); or
(a weight for medication/100×a quantity of medication(s) per treatment).

20. The computer-storage media of claim 19, wherein the computer-executable instructions are further configured to calculate the weighted scores by additionally summing one or more of:
(a weight for a reported side effect/(100×a major value+ 100×a moderate value+10×a minor value));
(a weight for an effectiveness score×an effectiveness value/1000);
(a weight for a physician response/(100×an accept response value+100×an override response value)); or
((a medication appropriateness score/100)−(a quantity of ordered occurrences of a medication per a particular diagnosis/a total quantity of medications ordered per that particular diagnosis)).

* * * * *